United States Patent [19]

Darms et al.

[11] Patent Number: 4,609,741
[45] Date of Patent: Sep. 2, 1986

[54] PHTHALIC ACID DERIVATIVES WHICH ARE SUBSTITUTED BY 2-PROPYNYLOXY GROUPS, PROCESSES FOR THEIR PREPARATION AND THEIR USE

[75] Inventors: Roland Darms, Therwil; Vratislav Kvita, Reinach; Charles E. Monnier, Villars-sur-Glâne, all of Switzerland

[73] Assignee: Ciba-Geigy Corporation, Ardsley, N.Y.

[21] Appl. No.: 639,048

[22] Filed: Aug. 9, 1984

[30] Foreign Application Priority Data

Aug. 18, 1983 [CH] Switzerland ............... 4513/83

[51] Int. Cl.$^4$ .................. C07D 209/48; C07D 307/89
[52] U.S. Cl. .................... 549/241; 548/473; 548/480; 548/461; 562/473
[58] Field of Search .......... 548/473, 480, 461; 562/473; 549/241, 243

[56] References Cited

U.S. PATENT DOCUMENTS

| | | | |
|---|---|---|---|
| 4,140,703 | 2/1979 | Darms et al. | 549/243 |
| 4,158,662 | 6/1979 | Darms et al. | 548/480 |
| 4,363,917 | 12/1982 | Fischer et al. | 549/243 |
| 4,459,414 | 7/1984 | Fischer et al. | 548/473 |

Primary Examiner—John Kight
Assistant Examiner—Nathan M. Nutter
Attorney, Agent, or Firm—Harry Falber

[57] ABSTRACT

Novel phthalic acid derivatives are described which are substituted by 2-propynyloxy groups, of the formula I

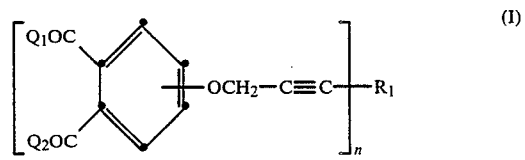

in which $Q_1$, and $Q_2$ independently of one another are —OH or —O$^-$M$^+$, or $Q_1$ and $Q_2$ together form the grouping —O—, [O$^-$]$_2$M$_1^{++}$ or —N(R$_2$)—, M$^+$ is an alkali metal ion, a trialkyl ammonium ion having 3–24 carbon atoms or a quaternary ammonium ion and M$_1^{++}$ is an alkaline earth metal ion, R$_2$ is an alkyl group or an unsubstituted or substituted aryl group, n is 1 or 2 and R$_1$ is hydrogen, if n is 1, or a direct bond, if n is 2, are described. The phthalic anhydrides which are substituted by 2-propynyloxy, of the formula I, can be used for curing epoxy resins, cured products with outstanding physical properties being obtained.

8 Claims, No Drawings

PHTHALIC ACID DERIVATIVES WHICH ARE SUBSTITUTED BY 2-PROPYNYLOXY GROUPS, PROCESSES FOR THEIR PREPARATION AND THEIR USE

The present invention relates to novel phthalic acid derivatives, in particular phthalic anhydrides, which are substituted by 2-propynyloxy groups, a process for their preparation and the use of the phthalic acid anhydrides which are substituted by 2-propynyloxy groups for curing epoxy resins.

The novel phthalic acid derivatives are those of the formula I

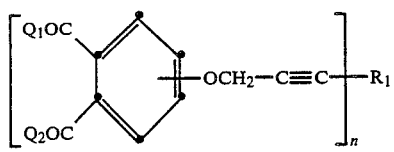

in which $Q_1$ and $Q_2$ independently of one another are —OH or —O$^-$M$^+$, or $Q_1$ and $Q_2$ together form the grouping —O—, —EO$^-$]$_2$M$_1^{++}$ or —N(R$_2$)—, M$^{30}$ is an alkali metal ion, a trialkylammonium ion having 3–24 carbon atoms or a quaternary ammonium ion and $M_1^{++}$ is an alkaline earth metal ion, $R_2$ is an alkyl group or a substituted or unsubstituted aryl group, n is 1 or 2 and $R_1$ is hydrogen, if n is 1, or a direct bond, if n is 2.

The phthalic acid derivatives of the formula I can also be in the form of mixtures of 3- and 4-isomers.

The phthalic acid derivatives of the formula I can be obtained, for example, by reacting a phthalimide of the formula II

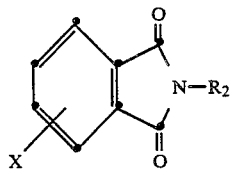

with a compound of the formula III $$HC\equiv C-CH_2-O^-M^+ \quad (III)$$

to give a phthalimide of the formula I'

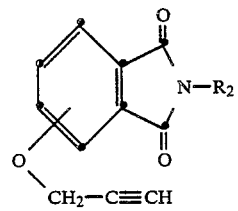

in which X is a nitro group or a halogen atom and $R_2$ and M$^+$ are as defined above, and, if appropriate, subsequently carrying out one or more of the following operations:

(i) hydrolysis of phthalimides of the formula I in a basic medium, followed by reaction with an acid to give the corresponding phthalic acids, (ii) conversion of phthalic acids of the formula I into salts of the type defined, (iii) cyclisation of phthalic acids of the formula I to give the corresponding phthalic anhydrides and (iv) oxidative coupling of compounds of the formula I where n is 1 and $R_1$ is hydrogen to give compounds of the formula I where n is 2 and $R_1$ is a direct bond.

M$^+$ is, for example, the lithium, sodium, potassium, trimethylammonium, triethylammonium, methyldiethylammonium or tri-n-octylammonium ion. Examples of quaternary ammonium ions M$^+$ are the benzyltrimethylammonium and the tetramethylammonium ion. M$^+$ is preferably the sodium ion.

Examples of alkaline earth metal ions $M_1^{++}$ are the calcium and magnesium ions.

Examples of halogen atoms X are fluorine, chlorine, bromine and iodine.

The groupings —[O—CH$_2$—C≡C]$_n$—R$_1$ (formula I) and the nitro group or halogen atom (formula II) are preferably in the 3-position of the benzene ring. $Q_1$ and $Q_2$ preferably have the same meaning.

Preferred phthalic acid derivatives of the formula I are those in which $Q_1$ and $Q_2$ together form a grouping —N(R$_2$)— and in which $R_2$ is a $C_{1-6}$-alkyl group, or is a $C_{6-12}$-aryl group which is unsubstituted or substituted by a $C_{1-6}$-alkyl, $C_{1-6}$-alkoxy or di-$C_{1-6}$-alkylamino group, in particular those in which $R_2$ is methyl or phenyl.

Compounds of the formula I in which $Q_1$ and $Q_2$ together form the grouping —O— are particularly preferred.

Starting substances of the formula II in which X is a nitro group are preferably used.

The starting substances of the formulae II and III are known per se or can be prepared in a manner which is known per se. Salts of the formula III can be used as such; however, they are preferably formed in situ from 2-propynol and alkali metal alcoholates, in particular sodium methylate or potassium methylate. The starting substances are advantageously reacted with one another in a polar medium, in particular in dimethyl sulfoxide (DMSO) or dioxane or mixtures thereof at temperatures between about 0° and 50° C., in particular about 15° and 30° C.

When the reaction has ended, the phthalimide formed of the formula I' can be precipitated by addition of aqueous mineral acid, such as aqueous hydrochloric acid or aqueous sulfuric or phosphoric acid, and, if appropriate, then subjected to one or more of the abovementioned additional operations. These operations can be carried out, for example, as shown in the equations below:

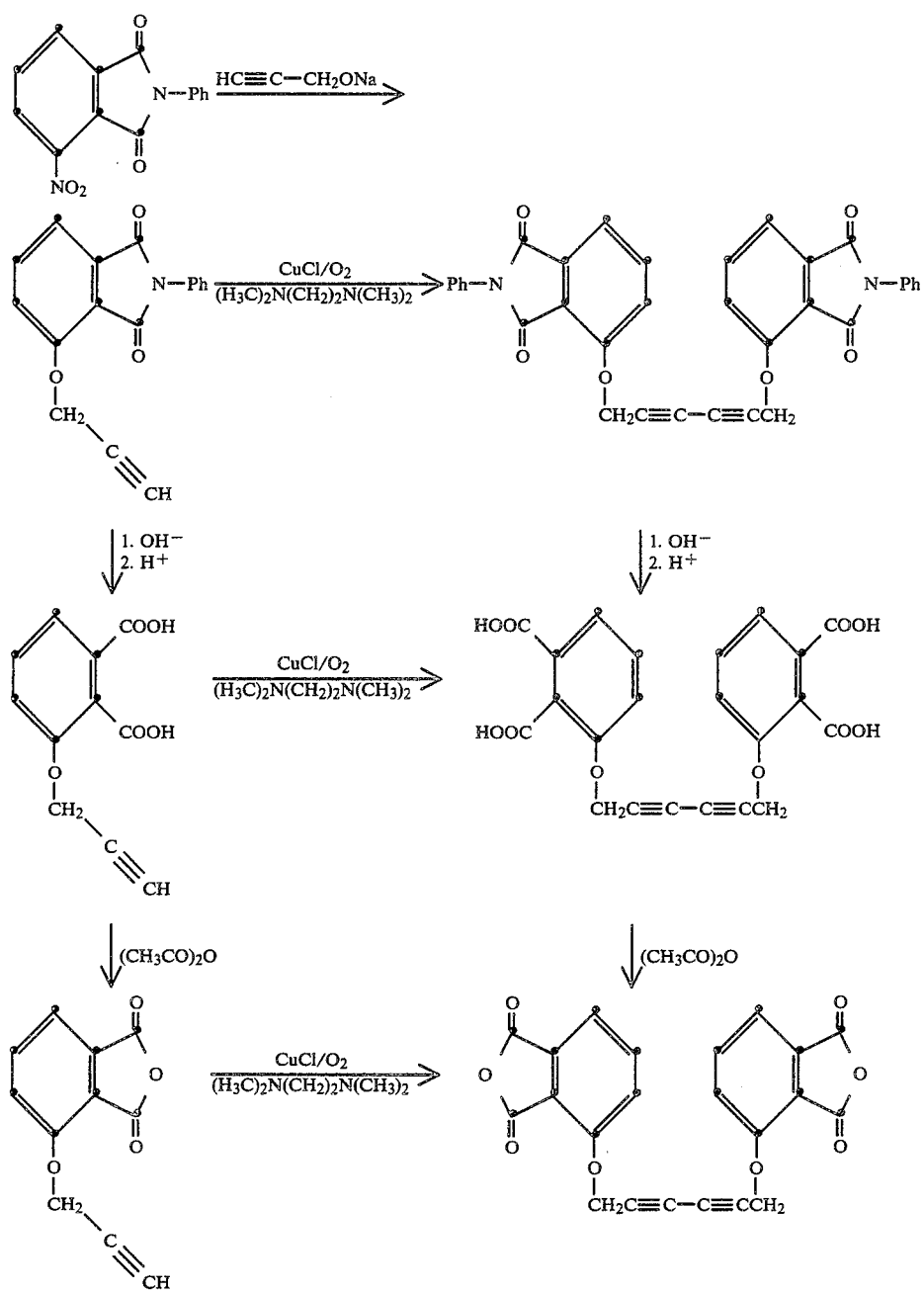

Compounds of the formula I (n is 1, $R_1$ is H) can be converted into bis-compounds of the formula I (n is 2, $R_1$ is a direct bond), for example, by oxidative coupling (see, for example, J. Org. Chem. 27, 3320 (1962)). The reaction is carried out in the presence of copper salts, for example copper-I chloride, oxygen and ammonia or amines, in particular tertiary or bidentate tertiary amines, preferably in polar aprotic solvents, for example tetrahydrofuran, dioxane, acetone, N,N-dimethylformamide, N,N-dimethylacetamide, dimethylsulfoxide or mixtures thereof, at temperatures between about 10° and 60° C., in particular between about 20° and 50° C.

Phthalimides of the formula I ($Q_1$ and $Q_2$ together are —N($R_2$)—) can also be converted into the corresponding substituted phthalic acid of the formula I ($Q_1$ and $Q_2$ are —OH) by basic hydrolysis, for example with sodium hydroxide, followed by reaction with mineral acid.

The conversion of the phthalic acids of the formula I ($Q_1$ and $Q_2$ are —OH) into the corresponding phthalic acid salts of the formula I, for example alkali metal or tri-or tetra-alkylammonium salts ($Q_1$ and $Q_2$ are identical and are —O$^-$M$^+$) or alkaline earth metal salts ($Q_1$ and $Q_2$ together are —[O$^-$]$_2$M$_1^{++}$), can be carried out in a manner which is known per se to the person skilled in the art.

Finally, the cyclisation of phthalic or bisphthalic acids to give anhydrides of the formula I ($Q_1$ and $Q_2$ together are —O—) can be carried out chemically or by means of heat in a manner which is known per se.

Chemical cyclisation is advantageously carried out at temperatures from about 15° to 130° C. in the presence of customary dehydrating agents. Dehydrating agents are, in particular, anhydrides of aliphatic monocarboxylic acids which have 2–5 carbon atoms and are unsubstituted or substituted by halogen atoms or alkyl groups, such as acetic anhydride, propionic anhydride or trifluoro-, trimethyl- or triethyl-acetic anhydride.

The compounds of the formula I according to the invention can be isolated and purified in the customary manner, for example by precipitation with aqueous acids as defined above, or by extraction or recrystallisation from suitable solvents, for example from dioxane, alcohols or water.

(2'-Propynyloxy) phthalic anhydrides of the formula I according to the invention ($Q_1$ and $Q_2$ together are —O—) are suitable curing agents for epoxy resins. Products or materials cured with these compounds have good mechanical and/or electrical properties, in particular a high crosslinking density and a high heat distortion temperature.

The present application thus also relates to curable mixtures which are suitable for the production of shaped articles, impregnations, coatings, cementings and the like. These mixtures contain (a) one or more polyepoxy compounds, (b) at least one compound of the formula I in which $Q_1$ and $Q_2$ together form the grouping —O— and n and $R_1$ are as defined above, as the curing agent, and (c) if appropriate, further additives.

Advantageously, if n is 1 and $R_1$ is H, 0.3 to 1.3 moles, preferably about 0.50 to 1.0 mole, of a phthalic anhydride of the formula I or, if n is 2 and $R_2$ is a direct bond, 0.15 to 0.70 mole, preferably 0.25 to 0.50 mole, of a diphthalic dianhydride of the formula I are used per equivalent of epoxy group of the polyepoxy compound (a).

Polyepoxy compounds (a) are all those which can be cured with anhydride curing agents. Particular examples are: alicyclic polyepoxides, such as epoxyethyl-3,4-epoxycyclohexane (vinylcyclohexene diepoxide), limonene diepoxide, dicyclopentadiene diepoxide, bis-(3,4-epoxycyclohexylmethyl) adipate, 3',4'-epoxycyclohexylmethyl 3,4-epoxycyclohexanecarboxylate, 3',4'-epoxy-6'-methylcyclohexylmethyl 3,4-epoxy-6-methylcyclohexanecarboxylate, 3-(3',4'-epoxycyclohexyl)-2,4-dioxaspiro[5,5]-8,9-epoxyundecane and 3-glycidyloxyethoxyethyl-2,4-dioxaspiro[5,5]-8,9-epoxyundecane; di- or poly-glycidyl ethers of polyhydric alcohols, such as 1,4-butanediol or polyalkylene glycols, such as polypropylene glycols, di- or poly-glycidyl ethers of cycloaliphatic polyols, such as 2,2-bis-(4-hydroxycyclohexyl)-propane, di- or poly-glycidyl ethers of polyhydric phenols, such as resorcinol, bis-(p-hydroxyphenyl)-methane (bisphenol F), 2,2-bis-(p-hydroxyphenyl)-propane (bisphenol A), 2,2-bis-(4'-hydroxy-3',5'-dibromophenyl)-propane or 1,1,2,2,-tetrakis(p-hydroxyphenyl)-ethane, or condensates of phenols and formaldehyde obtained under acid conditions, such as phenol novolaks and cresol novolaks; and furthermore di- or poly-(β-methylglycidyl) ethers of the above polyalcohols and polyphenols; polyglycidyl esters and poly(β-methylglycidyl) esters of polybasic carboxylic acids, such as phthalic acid, terephthalic acid, tetrahydrophthalic acid and hexahydrophthalic acid; N-glycidyl derivatives of amines, amides and heterocyclic nitrogen bases, such as N,N-diglycidylaniline, N,N-diglycidyltoluidine, N,N,N',N'-tetraglycidyl-bis-(p-aminophenyl)methane, triglycidylisocyanurate, N,N'-diglycidylethyleneurea, N,N'-diglycidyl-5,5-dimethylhydantoin, N,N'-diglycidyl-5-isopropylhydantoin and N,N'-diglycidyl-5,5-dimethyl-6-isopropyl-5,6-dihydrouracil.

If desired, active diluents, for example styrene oxide, butylglycidyl ether, 2,2,4-trimethylpentylglycidyl ether, phenylglycidyl ether, cresylglycidyl ether, glycidyl esters of synthetic, highly branched, mainly tertiary aliphatic monocarboxylic acids can be added to the curable mixtures in order to reduce the viscosity.

Curing accelerators can also be used during curing; examples of accelerators are tertiary amines, salts thereof or quaternary ammonium compounds, for example benzyldimethylamine, 2,4,6-tris-(dimethylaminomethyl)-phenol, 1-methylimidazole, 2-ethyl-4-methylimidazole, 4-aminopyridine and tripentylammonium phenolate; and alkali metal alcoholates, for example sodium hexanetriolate. Curing of the mixtures according to the invention is advantageously carried out in the temperature range from 50° C. to 300° C., preferably from 80° to 250° C.

Curing can also be carried out in two or several stages in a known manner, the first curing stage being carried out at a low temperature and after-curing being carried out at a higher temperature.

If desired, curing can also be carried out in 2 stages such that the curing reaction is initially interrupted prematurely, or the first stage is carried out at a slightly elevated temperature, a curable precondensate, which is still fusible and/or soluble (the so-called "B-stage"), being obtained from the epoxy component (a) and the curing agent (b). Such a precondensate can be used, for example, for the production of "prepregs", moulding compositions or sintering powders.

The expression "curing" as used here means the conversion of the soluble, either liquid or fusible polyepoxides into solid, insoluble and infusible, three-dimensional crosslinked products or materials, in particular, as a rule, with simultaneous shaping to shaped articles, such as cast articles, pressed articles and laminated materials, and to impregnations, coatings, varnish films or cementings.

The mixtures according to the invention can contain, in particular, unsaturated bis-imidyl derivatives as further additives (c).

Examples of unsaturated bis-imidyl derivatives which can be used are those of the formula IV

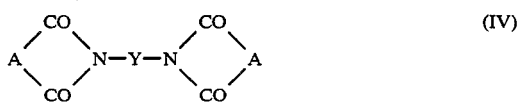 (IV)

in which Y is a divalent bridge member having 2–30 carbon atoms and A is

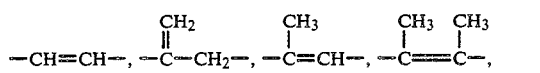

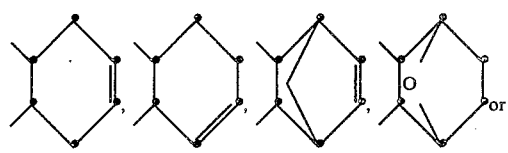 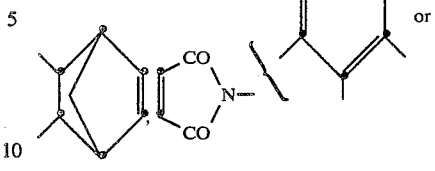

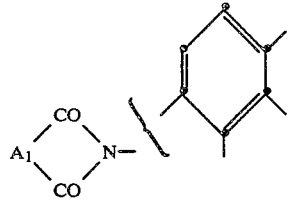

in which $A_1$ can have the same meanings as A, with the exception of the last meaning mentioned.

A bridge member Y is, in particular, a straight-chain or branched group of the formula —$C_pH_{2p}$—, in which p is 2–12, in particular 2–6, or a phenylene or naphthylene group which is unsubstituted or substituted by halogen atoms, such as chlorine, fluorine or bromine, or by alkyl or alkoxy groups having 1–4, in particular 1 or 2, carbon atoms, or a cyclohexylene group or a group of the formula

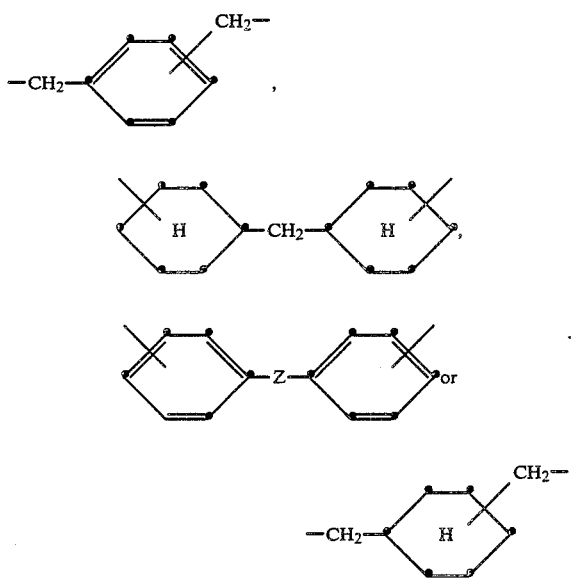

in which Z is —$CH_2$—, —O—, —S—, —SO—,

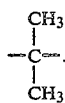

Particularly preferred compounds of the formula IV are those in which A is a group of the formula —CH=CH—,

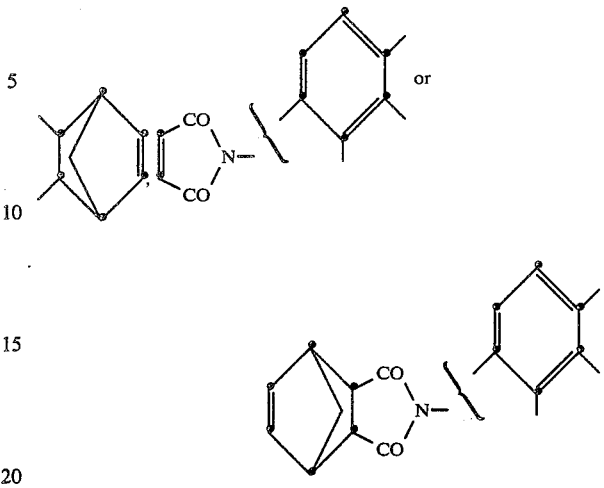

and Y is a 4,4′-diphenylmethane or 4,4′-diphenyl ether radical.

The processing properties of the curable mixtures according to the invention can be altered by addition of compounds of the formula IV and novel useful modifications of the physical properties of the cured shaped articles obtainable with these mixtures can be achieved. The compounds (c) mentioned are advantageously used in amounts of about 5–50 mole %, in particular about 10–35 mole %, based on the phthalic anhydride of the formula I.

The curable mixtures according to the invention can furthermore contain suitable plasticisers, such as dibutyl phthalate, dioctyl phthalate or tricresyl phthalate.

Finally, extenders, fillers and reinforcing agents, for example coal tar, bitumen, textile fibres, glass fibres, asbestos fibres, boron fibres, carbon fibres, mineral silicates, mica, quartz flour, hydrated aluminium oxide, bentonites, kaolin, silica aerogel or metal powders, for example aluminium powder or iron powder, and furthermore pigments and dyes, such as carbon black, oxide dyes, titanium dioxide and the like, can be added to the curable mixtures according to the invention in any phase before the curing. Moreover, other customary additives, for example flameproofing agents, such as antimony trioxide, thixotropic agents and flow control agents, such as silicones, waxes or stearates (which are partly also used as mould release agents) can also be added to the curable mixtures.

The curable mixtures according to the invention can be prepared in the customary manner with the aid of known mixing units (stirrers, kneaders, mills and the like).

The curable epoxy resin mixtures according to the invention are chiefly used in the fields of protection of surfaces, electrical engineering and laminating, and in civil engineering. They can be used in the particular formulation suited to the specific intended purpose, in the nonfilled or filled state, as paints or varnishes, as moulding compositions, immersion resins, casting resins, injection moulding formulations, impregnation resins and adhesives, and as tool resins, laminating resins, sealing and filling compositions and flooring compositions, and binders for mineral aggregates.

The following epoxy resin is used for the preparation of curable mixtures which is described in the use examples:

EPOXY RESIN A

An epoxy resin (technical grade product) which is prepared by condensation of 2,2-bis-(p-hydroxyphenyl)propane (bisphenol A) with a stoichiometric excess of epichlorohydrin in the presence of an alkali, chiefly consists of monomeric diglycidyl ether of the formula

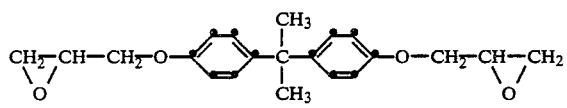

is liquid at room temperature and has an epoxide content of 5.12–5.54 epoxide equivalents/kg. The Hoeppler viscosity of the resin at 25° C. is 9,000–13,000 mPas.

PREPARATION EXAMPLES

EXAMPLE 1

N-Methyl-4-(2'-propynyloxy)phthalimide

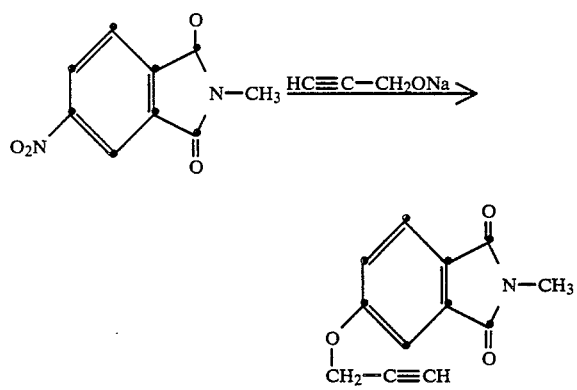

300 ml of analytical grade methanol are introduced into a 500 ml three-necked flask, with a thermometer, under $N_2$, and 4.8 g of metallic sodium are added in portions. The methanol is distilled off from the solution. 25.8 g (0.46 mole) of 2-propynol are added dropwise to the residue of sodium methylate at 10° C. and the mixture is stirred for 1 hour. The excess 2-propynol is distilled off at 13.3 Pa/25° C. and the residue is taken up in 80 ml of dimethyl sulfoxide at 15° C. 34.0 g (0.16 mole) of N-methyl-4-nitrophthalimide in 60 ml of dioxane are added to this solution at 10°–15° C., under $N_2$. The reaction mixture is stirred at room temperature for 16 hours. The dark brown solution is stirred into 300 ml of 3% HCl. After about 2 hours, a brown precipitate separates out, and is filtered off, washed several times with water and dried at room temperature under 6.7 Pa.

19.90 g (57.8% of theory) of crystalline N-methyl-4-(2'-propynyloxy)phthalimide of melting point 128°–130° C. result. After recrystallisation from methanol, the melting point rises to 135°–137° C.

IR (KBr): 3240, 2220, 1760, 1700, 1610, 1490, 1450, 1430, 1370, 1350, 1270 and 1170 cm$^{-1}$.

$C_{12}H_{19}NO_3$ (215.20): calculated C 66.97% H 4.22% N 6.51%. Found C 66.32% H 4.17% N 6.84%.

EXAMPLE 2

N-Methyl-3-(2'-propynyloxy)phthalimide 120 ml of absolute methanol are introduced into a 500 ml 3-necked flask, and 2.4 g (0.104 mole) of sodium are added in portions. After the sodium has dissolved completely, the excess methanol is distilled off.

12.9 g (0.23 mole) of 2-propynol are then added dropwise at 5°–10° C., with cooling. The excess 2-propynol is distilled off at 20° C. under 13.3 Pa. The residue is dissolved in 25 ml of dimethyl sulfoxide; 17.0 g (0.08 mole) of N-methyl-4-nitrophthalimide in 70 ml of dimethyl sulfoxide are then added dropwise, whereupon a dark violet, thick suspension is formed. The reaction mixture is stirred for 20 hours and the solid is filtered off, washed several times with methanol and then stirred into 300 ml of 3% HCl. After about 3 hours, the precipitate is filtered off with suction, washed neutral with deionised water and dried. 9.90 g (57.5% of theory) of N-methyl-3-(2'-propynyloxy)phthalimide of melting point 172°–174° C. result as colourless crystals.

IR (KBr): 3300, 2250, 1790, 1720, 1640, 1490, 1440, 1420, 1370, 1350, 1270, 1250, 1170, 1070, 1050, 990 and 970 cm$^{-1}$.

NMR (d-DMSO) δ [ppm]: 3.0 s 3H (—CH$_3$); 3.65 t 1H (J=2 Hz) (≡CH); 5.02 d 2H (J=2 Hz) (—OCH$_2$—); and 7.2–7.8 m 3H (phenyl-H).

$C_{12}H_{19}NO_3$ (215.20): Calculated C 66.97% H 4.22% N 6.51%. Found C 66.88% H 4.22% N 6.48%.

EXAMPLE 3

N-Phenyl-4-(2'-propynyloxy)phthalimide 6.63 g (0.28 mole) of metallic sodium are dissolved in 150 ml of absolute methanol in a 500 ml 3-necked flask with a magnetic stirrer. The excess of methanol is distilled off, whereupon white sodium methylate precipitates. 44.7 g (0.79 mole) of 2-propynol are then added at 10°–20° C. (exothermic reaction), under nitrogen. The excess 2-propynol is distilled off at 10°–20° C. (1.33 Pa). 150 ml of dimethyl sulfoxide are added to the light yellow, waxy residue, a clear, yellow solution being formed after 30 minutes. 60 g (0.22 mole) of 4-nitrophthalic acid N-phenylimide, in powder form or as a solution in dimethyl sulfoxide, are then added at 20° C. in the course of about 20 minutes, under $N_2$. The mixture is stirred at 15°–25° C. for 20 hours; the crude product is then filtered off with suction. The precipitate is washed with methanol and stirred into 300 ml of 1% HCl, the mixture is subsequently stirred for 30 minutes and then subsequently stirred in 300 ml of $H_2O$ for 20 hours, and the precipitate is filtered off with suction and dried at 25° C. under 1.33 Pa. 5.6 g (92% of theory) of N-phenyl-4-(2'-propynyloxy)phthalimide of melting point 169°–170° C. result as a light beige powder.

IR (KBr): 3200, 2240, 1780, 1720, 1620, 1480, 1450, 1400, 1380 and 1340 cm$^{-1}$.

NMR (d-DMSO) δ [ppm]: 3.65 ppm t 1H (J=2 Hz) (≡CH); 5.05 d 2H (J=2 Hz) (—OCH₂); and 7.2-7.9 m 3+5H (phenyl-H of the phthalic acid+phenyl-H).

EXAMPLE 4

N-Phenyl-3-(2'-propynyloxy)phthalimide

N-phenyl-3-(2'-propynyloxy)phthalimide is prepared in a similar manner to N-phenyl-4-(2'-propynyloxy)phthalimide. 60.0 g (0.22 mole) of 3-nitro-N-phenylphthalimide are used instead of the 4-nitro-N-phenylphthalimide.

26.70 g (43.8% of theory) of N-phenyl-3-(2'-propynyloxy)phthalimide result, and are recrystallised from ethanol to give colourless, cottonwool-like crystals of melting point 167°-168° C.

IR (KBr): 3200, 2240, 1760, 1720, 1610, 1510 and 1490 cm⁻¹.

NMR (d-DMSO) δ [ppm]: 3.62 t 1H (J=2 Hz) (≡CH), 5.02 d 2H (J=2 Hz) (—O—CH₂—); and 7.2-7.8 5+3H (phenyl-H+phenyl-H of the phthalic acid)

$C_{17}H_{11}NO_3$ (277.28): Calculated C 73.64% H 4.00% N 5.00%. Found C 73.85% H 4.08% N 5.17%.

EXAMPLE 5

4-(2'-Propynyloxy)phthalic acid

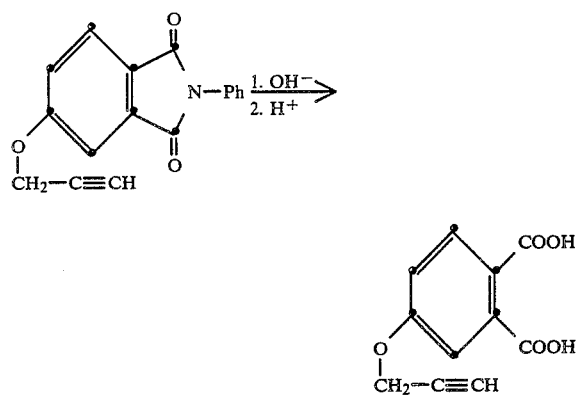

15.0 g (0.05 mole) of N-phenyl-4-(2,'-propynyloxy)phthalimide in 200 ml of 20% NaOH are introduced into a 750 ml sulfonating flask with a stirrer and condenser. The reaction mixture is stirred at 25° C. for 2 hours, at 35° C. for 36 hours and at 70° C. for 4 hours. When the stirring has ended, 150 ml of 18% HCl are added dropwise at 50° C., followed by 150 ml of water. The reaction mixture is subsequently stirred at 100° C. for another 5 hours and is then filtered hot, and the filtrate is allowed to cool. The precipitate which has separated out is filtered off and the crude product is recrystallised from 50% aqueous 1-propenol. 7.0 g (59% of theory) of 4-(2'-propynyloxy)phthalic acid of melting point 180°-181° C. result as colourless crystals.

IR (KBr): 3500-3300, 2220, 1680, 1600 and 1420 cm⁻¹.

NMR (d-DMSO) δ [ppm]: 3.4 ppm t 1H (J=2 Hz) (≡CH); 4.8 ppm d 2H (J=2 Hz) (—OCH₂—); 7.0-7.6 ppm m 3H phenyl-H and 9.5-10.5 2H (—COOH).

EXAMPLE 6

3-(2'-Propynyloxy)-phthalic acid

A 13.0 g (0.046 mole) of N-phenyl-3-(2'-propynyloxy)phthalimide and 150 ml of 15% sodium hydroxide solution are warmed at 50° C. for 2 hours and then at 70° C. for a further 2 hours in a 750 ml sulfonating flask. The clear reddish solution thereby formed is cooled to ~10° C.; 150 ml of 17% HCl are then added dropwise in the course of 50 minutes. The resulting precipitate is filtered off with suction, the crude product is stirred again into 100 ml of 17% HCl and the mixture is subsequently stirred at 110° C. for 60 minutes. After cooling, brown crystals precipitate and are filtered off and dried. 7.3 g (71% of theory) of 3-(2'-propynyloxy) phthalic acid result. Recrystallisation from water gives colourless needles of melting point 193°-195° C.

IR (KBr): 3500-3300, 2240, 1820, 1780, 1600 and 1500 cm⁻¹.

NMR (d-DMSO) [ppm]: 3.5 t 1H (J=2 Hz) (≡CH); 4.8 d 2H (J=2 Hz) (—OCH₂—); and 7.2-7.6 m 3H (phenyl-H).

$C_{11}H_8O_5$ (220.18): Calculated C 60.01% H 3.66%. Found C 60.03% H 3.70%.

EXAMPLE 7

Hay oxidative coupling of N-methyl-4-(2'-propynyloxy)phthalimide to give 4,4'-(hexa-2",4"-diynylenedioxy)-di-N-methylphthalimide

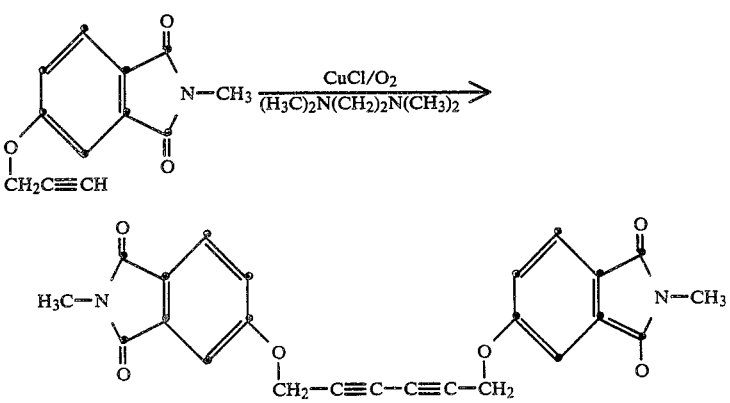

100 ml of acetone, 0.75 g (0.0075 mole) of Cu-I chloride and 3.9 g (0.075 mole) of N,N,N',N'-tetramethylethylenediamine are introduced into a 500 ml three-necked flask with an $O_2$ inlet. A solution of 2.0 g (0.009 mole) of N-methyl-4-(2'-propynyloxy)-phthalimide in 20 ml of dioxane and 20 ml of acetone is added dropwise, while passing in oxygen. The reaction mixture is stirred at 20°–25° C. for 1 hour and at 40° C. for 4 hours. When the reaction has ended, the reaction mixture is cooled to 5°–10° C. and 20 ml of 2N HCl and 150 ml of water are added dropwise in succession, whereupon the dimer of the above formula precipitates. After filtration and drying, 1.9 g (95% of theory) of white to greenish crystals of melting point 230°–232° C. are obtained.

IR (KBr): 1770, 1700, 1620, 1450, 1390, 1290, 1220 and 1110 $cm^{-1}$.

$C_{24}H_{16}N_2O_6$ (428.40): Calculated C 67.29% H 3.77% N 6.54%. Found C 47.1% H 3.8% N 6.4%.

EXAMPLE 8

Hay oxidative coupling of N-methyl-3-(2'-propynyloxy)-phthalimide to give 3,3'-(hexa-2'',4'''-diynylenedioxy)-di-N-methylphthalimide 4.45 g (0.045 mole) of Cu-I chloride and 5.22 g (0.045 mole) of N,N,N',N'-tetramethylethylenediamine in 300 ml of acetone are introduced into a 1000 ml three-necked flask with an oxygen inlet tube. A solution of 10.2 g (0.047 mole) of N-methyl-3-(2'-propynyloxy)-phthalimide in 40 ml of dioxane, 40 ml of acetone and 60 ml of N,N-dimethylformamide is added dropwise at 20°–30° C. in the course of 30 minutes, during which the reaction mixture is stirred vigorously, while passing in oxygen. After a further reaction time of 14 hours, the reaction mixture is cooled to 5° C. and 100 ml of 2N HCl are added dropwise. The precipitate thereby formed is filtered off with suction, washed until neutral and dried. 9.5 g (93% of theory) of a light green powder of melting point 228°–230° C. result.

IR (KBr): 3800, 3060, 1780, 1680, 1600, 1490, 1430, 1380, 1280, 1250, 1080 and 1050 $cm^{-1}$.

$C_{24}H_{16}N_2O_6$ (428.40):Calculated C 67.29% H 3.77% N 6.54%. Found C 66.90% H 4.1% N 6.5%.

EXAMPLE 9

Hay oxidative coupling of N-phenyl-3-(2'-propynyloxy)-phthalimide to give 3,3'-(hexa-2'',4'''-diynylenedioxy)-di-N-methylphthalimide 300 ml of acetone, 2.76 g (0.028 mole) of Cu-I chloride and 3.24 g (0.028 mole) of N,N,N',N'-tetramethylethylenediamine are introduced into a 500 ml three-necked flask with an oxygen inlet tube. 11.08 g (0.04 mole) of N-phenyl-3-(2'-propynyloxy)-phthalimide are then added and oxygen is passed in at 35° C. for 6 hours, with intensive stirring. When the reaction has ended, 80 ml of 2N HCl are added dropwise at 25° C., whereupon the dimer precipitates. After filtration and drying, 11.0 g (99% of theory) of the dimeric phthalimide of melting point 218°–220° C. are obtained. After recrystallisation from dioxane, yellow crystals of melting point 228°–230° C. are obtained.

IR (KBr): 3600, 3080, 1770, 1700, 1630, 1470, 1430, 1370, 1280, 1100 and 1030 $cm^{-1}$.

$C_{34}H_{20}N_2O_6$ (552.54): Calculated C73.91% H 3.65% N 5.07%. Found C74.1% H 4.0% N 5.1%.

EXAMPLE 10

Hay oxidative coupling of 4-(2'-propynyloxy)phthalic acid to give 4,4'-(hexa-2'',4'''-diynylenedioxy)diphthalic acid 150 ml of tetrahydrofuran, 5.94 g (0.06 mole) of Cu-I chloride and 6.97 g (0.06 mole) of N,N,N',N'-tetramethylethylenediamine are introduced into a 500 ml round-bottomed flask with a gas inlet tube. A solution of 3.0 g (0.014 mole) of 4-(2'-propynyloxy)-phthalic acid in 30 ml of dimethylformamide is added dropwise, while passing in $O_2$, and the mixture is stirred at 20° C. for 72 hours. When the reaction has ended, the reaction mixture is concentrated to about 1/5 of the volume at 40° C. and 500 ml of water are then added. The resulting precipitate is filtered off, washed with water and dried in vacuo. 2.8 g (93% of theory) of the abovementioned diphthalic acid result as a grey-white powder which decomposes at 158°–160° C.

IR (KBr): 3500–3300, 2260, 1705, 1670, 1600, 1430 and 1370 $cm^{-1}$.

Molecular weight determination: Calculated 438.34. Found 433.

EXAMPLE 11

Hay oxidative coupling of 3-(2'-prooynyloxy)phthalic acid to give 3,3'-(hexa-2'',4'''-diynylenedioxy)diphthalic acid 500 ml of absolute tetrahydrofuran, 15 ml of dimethylformamide, 15.5 g (0.16 mole) of Cu-I chloride and 18.6 g (0.16 mole) of N,N,N',N'-tetramethylethylenediamine are introduced into a 750 ml sulfonating flask with an oxygen inlet tube. A solution of 7.93 g (0.036 mole) of 3-(2'-propynyloxy)phthalic acid in 30 ml of dimethylformamide is added dropwise to the solution at 20° C. in the course of 10 minutes, oxygen being passed in at the same time. The mixture is stirred at room temperature for 36 hours. After working up as in the case of the 4,4'-isomer, 6.7 g (84% of theory) of reddish-violet crystals of melting point 192°–195° C. result.

IR (KBr): 3500, 3300, 1725, 1680, 1460 and 1300 $cm^{-1}$.

$C_{22}H_{14}O_{10}$ (438.34): Calculated C 60.28% H 3.22%. Found C 59.1% H 3.7%.

EXAMPLE 12

4-(2'-Propynyloxy)phthalic anhydride 10.0 g (0.045 mole) of 4-(2'-propynyloxy)phthalic acid and 100 ml of acetic anhydride are introduced into a 250 ml three-necked flask with a magnetic stirrer, condenser and thermometer and the mixture is warmed at 110°–120° C. for 60 minutes. When the reaction has ended, the reaction mixture is concentrated in vacuo and the residue is recrystallised from toluene and petroleum ether. 5.6 g (61% of theory) of yellow 4-(2'-propynyloxy)phthalic anhydride of melting point 83°–84° C. result. A further 1.70 g (18.5% of theory) of anhydride are obtained from the mother liquor.

IR (KBr): 3260, 1830, 1770, 1620, 1600, 1480, 1450, 1290 and 1260 cm$^{-1}$.

NMR (d-DMSO) δ [ppm]: 3.70 t 1H, (J=2 Hz) (—C≡CH); 5.1 d 2H (J=2 Hz) (—O—CH$_2$—); and 7.35–8.01 m 3H (phenyl-H).

EXAMPLE 13

3-(2'-Propynyloxy)phthalic anhydride 50 ml of acetic anhydride and a spatula-tip of active charcoal are added to 7.3 g (0.03 mole) of 3-(2'-propynyloxy)phthalic acid in a 100 ml round-bottomed flask with a condenser, and the mixture is warmed at 110° C. for 30 minutes. After filtration, the filtrate is cooled and, after cooling to about 5° C., colourless crystals are filtered off with suction, washed and dried. 3.0 g (49.46% of theory) of 3-(2'-propynyloxy)phthalic anhydride result as colourless crystals of melting point 162°–165° C.

IR (KBr): 3400, 2250, 1850, 1620 and 1470 cm$^{-1}$.

NMR (d-DMSO) δ [ppm]: 3.6 t 1H (J=2 Hz) (≡CH); 5.01 d 2H (J=2 Hz) (—OCH$_2$—); and 7.3–8.0 m 3H (phenyl-H).

$C_{11}H_6O_4$ (202.17): calculated C 65.35% H 2.99% O 31.66%. Found C 65.1% H 2.8% O 32.0%.

EXAMPLE 14

4,4'-(Hexa-2",4"-diynylenedioxy)diphthalic acid dianhydride 1.0 g (0.0023 mole) of the tetracarboxylic acid prepared according to Example 10 is dissolved in 20 ml of toluene and 5 ml of acetic anhydride and the solution is stirred at room temperature for 48 hours. The solvent is distilled off and the residue is recrystallised from toluene/active charcoal and dried.

0.5 g (55% of theory) of ochre-coloured, pulverulent dianhydride of melting point 196°–198° C. result.

IR (KBr): 3120, 1850, 1780, 1600, 1490, 1280, 1080, 1000, 730 and 700 cm$^{-1}$.

NMR (d-DMSO) δ [ppm]: 5.1 s 4H (—OCH$_2$—), and 7.1–8.0 m 6H (phenyl-H).

$C_{22}H_{10}O_8$ (402.32): Calculated C 65.36% H 2.5%. Found C 65.00% H 2.9%.

EXAMPLE 15

3,3'-(Hexa-2",4"-diynylenedioxy)diphthalic acid dianhydride 6.3 g (0.014 mole) of the tetracarboxylic acid prepared according to Example 11 are dissolved in a mixture of 50 ml of acetic anhydride, 600 ml of acetone and 100 ml of toluene in a 1 liter round-bottomed flask and the solution is kept at 50°–60° C. for 2 hours. The reaction mixture is filtered and the filtrate is cooled to 5°–10° C., whereupon the anhydride precipitates. After washing and drying, 5.3 g (92% of theory) of dianhydride are obtained as light brown crystals of melting point 232°–234° C. Colourless crystals of melting point 233° C. are obtained on recrystallisation from dioxane.

IR (KBr): 3030, 2860, 2250, 1820, 1750, 1570, 1470, 1270, 1190, 1050 and 895 cm$^{-1}$.

NMR (d-DMSO):δ [ppm]: 5.30 s 4H (—O—CH$_2$—) and 7.3–8.1 m 6H (phenyl-H).

$C_{22}H_{10}O_8 \cdot C_4H_8O_2$ (490.4): Calculated C 63.67% H 3.67% O 32.65%. Found C 63.77% H 3.66% O 32.49%.

USE EXAMPLES I–IV

In each case 100 parts by weight of epoxy resin A (bisphenol A diglycidyl ether) and 0.05 part by weight of benzyldimethylamine (curing accelerator) are mixed with 91.6 parts by weight of the particular anhydride, as a curing promoter. The reactivity of these mixtures, on the one hand, is determined by means of differential thermal analysis (DTA), and, on the other hand, the glass transition temperature (TG) of the cured products is determined.

(a) DIFFERENTIAL THERMAL ANALYSIS (DTA)

Differential thermal analysis is used to determine the reactivity. About 20 mg of resin/curing agent mixture to be tested are warmed in a small Al crucible in the measurement chamber of a DTA apparatus (TA 2000, Mettler, Greifensee, Switzerland) with a heating-up rate of 4° C./minute, and the temperature difference from an empty crucible warmed at the same time is continuously recorded. The temperatures for the start of the reaction ($T_S$), for the maximum rate of reaction ($T_{RRmax}$) and for the end of the reaction ($T_E$) are given from the resulting curve as parameters which characterise the reactivity. The enthalpy of reaction is calculated from the area between the resulting curve and the baseline. The results of the measurements are shown in the table.

(b) DETERMINATION OF THE GLASS TRANSISTION TEMPERATURES ($T_G$)

In each case 2–4 g of the resin/curing agent mixture are poured into a thin-walled Al crucible about 1–4 cm in diameter and cured in this crucible. A sample of the disc thus obtained is removed in order to determine the glass transition temperature ($T_G$) of the crosslinked polymer with the aid of differential thermal analysis. At the transition point, the specific heat changes; this change is recorded as a turning point in the curve recorded by the DTA apparatus (TA 2000, Mettler, Greifensee, Switzerland). From the glass transition temperature, conclusions as to the heat distortion temperature of the resulting polymer can be drawn. The measurement values are shown in the table.

TABLE

| DTA | Example I<br>(anhydride with O-CH₂-C≡CH) | Example II<br>(anhydride with -O-CH₂-C≡CH) | Example III<br>(anhydride with O-CH₂-C≡C-C≡C-CH₂) | Example IV<br>(anhydride with O-CH₂-C≡C-C≡C-CH₂) |
|---|---|---|---|---|
| $T_S$ (°C) | 38 | 63 | 86 | 55 |
| | 141 | 182 | | 101 |
| $T_{RRmax}$ (°C) | 96 | 115 | 145 | 76 |
| | 261 | 266 | 285 + 374 | 144 + 207 + 283 |
| $T_E$ (°C) | 164 | 161 | 421 | 101 |
| | 312 | 309 | | 312 |
| Enthalpy of reaction per epoxide equivalent (kJ) | 68.52<br>132.52 | 106.13<br>166.26 | 203.9 | 3.9<br>147.9 |
| $T_G$ (°C) | 132[a]<br>157[b] | 161[b]<br>166[e] | 93 + 120[c]<br>130 + 164[d] | 59 + 87[c]<br>70[d] |

Curing cycles:
[a] 6 hours at 120° C., 2 hours at 180° C.
[b] 6 hours at 120° C., 2 hours at 180° C., 6 hours at 150° C.
[c] 4 hours at 80° C., 6 hours at 120° C.
[d] 4 hours at 80° C., 6 hours at 120° C., 6 hours at 180° C.
[e] 6 hours at 120° C., 6 hours at 180° C.

The data determined by differential thermal analysis indicates that in each case at least two different curing reactions take place, which can be explained by the polyfunctional character of the compounds of the formula I ($Q_1$ and $Q_2$ together are —O—), i.e. by their reactivity both on the anhydride ring and at the triple bond. The crosslinking caused by one or both of the abovementioned reactions is advanced to various stages, depending on the curing cycle used, which leads to different glass transition temperatures ($T_G$).

Cured epoxy resins with an exceptionally high heat distortion point (high $T_G$ values), which have a very advantageous effect in many possible uses, are obtained with the curing agents according to the invention.

What is claimed is:

1. A phthalic acid derivative of the formula I:

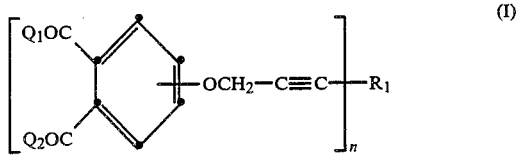

(I)

in which $Q_1$ and $Q_2$ independently of one another are —OH or —O$^-$M$^+$, or $Q_1$ and $Q_2$ together form the grouping —O—, —[O$^-$]$_2$M$_1^{++}$ or —N($R_2$)—, M$^+$ is an alkali metal ion, a trialkylammonium ion having 3–24 carbon atoms or a quaternary ammonium ion and M$_1^{++}$ is an alkaline earth metal ion, $R_2$ is an alkyl group or an unsubstituted or substituted aryl group, n is 1 or 2 and $R_1$ is hydrogen, if n is 1, or a direct bond, if n is 2.

2. A phthalic acid derivative of the formula I as claimed in claim 1, in which $Q_1$ and $Q_2$ together form a grouping —N($R_2$)— and in which $R_2$ is a $C_{1-6}$-alkyl group, or is a $C_{6-12}$-aryl group which is unsubstituted or substituted by a $C_{1-6}$-alkyl, $C_{1-6}$-alkoxy or di-$C_{1-6}$-alkylamino group.

3. A phthalic acid derivative of the formula I as claimed in claim 1, in, which $Q_1$ and $Q_2$ together form a grouping —N($R_2$)—, and in which $R_2$ is methyl or phenyl.

4. A phthalic acid derivative of the formula I as claimed in claim 1, in which $Q_1$ and $Q_2$ together form the grouping —O—.

5. A phthalic acid derivative of the formula I as claimed in claim 1, in which the grouping -[O—CH$_2$—C≡]$_n$-R$_1$ is in the 3-position of the benzene ring.

6. A phthalic acid derivative as claimed in claim 1, of the formula

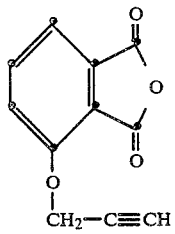

7. A phthalic acid derivative as claimed in claim 1, of the formula

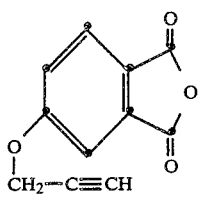

8. A phthalic acid derivative as claimed in claim 1, of the formula

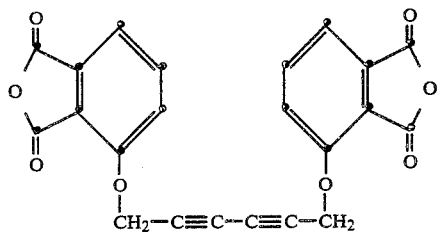

* * * * *